United States Patent [19]
Morrow et al.

[11] 3,960,673
[45] June 1, 1976

[54] TECHNIQUE FOR CONTINUOUSLY ANALYZING THE CONCENTRATION OF OZONE DISSOLVED IN WATER

[75] Inventors: James J. Morrow, Norristown; Leo L. Dailey, Philadelphia, both of Pa.

[73] Assignee: Fischer & Porter Co., Warminster, Pa.

[22] Filed: Sept. 27, 1974

[21] Appl. No.: 509,829

Related U.S. Application Data

[63] Continuation-in-part of Ser. No. 44,800, June 9, 1970, abandoned.

[52] U.S. Cl. .............................. 204/1 R; 204/195 R
[51] Int. Cl.² ......................................... G01N 27/46
[58] Field of Search .................... 204/1 T, 195 R

[56] References Cited
UNITED STATES PATENTS

| | | | |
|---|---|---|---|
| 2,651,612 | 9/1953 | Haller | 204/195 R |
| 2,861,926 | 11/1958 | Jacobson | 204/1 T |
| 3,038,848 | 6/1962 | Brewer et al. | 204/195 R |
| 3,043,764 | 7/1962 | Harvey | 204/195 R |
| 3,234,117 | 2/1966 | Rost et al. | 204/195 R |
| 3,449,233 | 6/1969 | Morrow | 204/195 R |
| 3,494,838 | 2/1970 | Chapron et al. | 204/1 T |

*Primary Examiner*—T. Tung

[57] ABSTRACT

A technique for continuously indicating the concentration of ozone dissolved in water, use being made of an amperometric cell, preferably formed of a gold cathode concentrically disposed within a tubular copper anode to define an annular passage, the cathode being rotated at high speed. A sample stream of the water is directed through the passage at a predetermined flow rate whereby in the absence of dissolved ozone, the cathode is polarized, but in the presence thereof, depolarization takes place to cause a current to flow in the cell, the current being measured to provide a reliable and continuous reading of ozone concentration.

5 Claims, 4 Drawing Figures

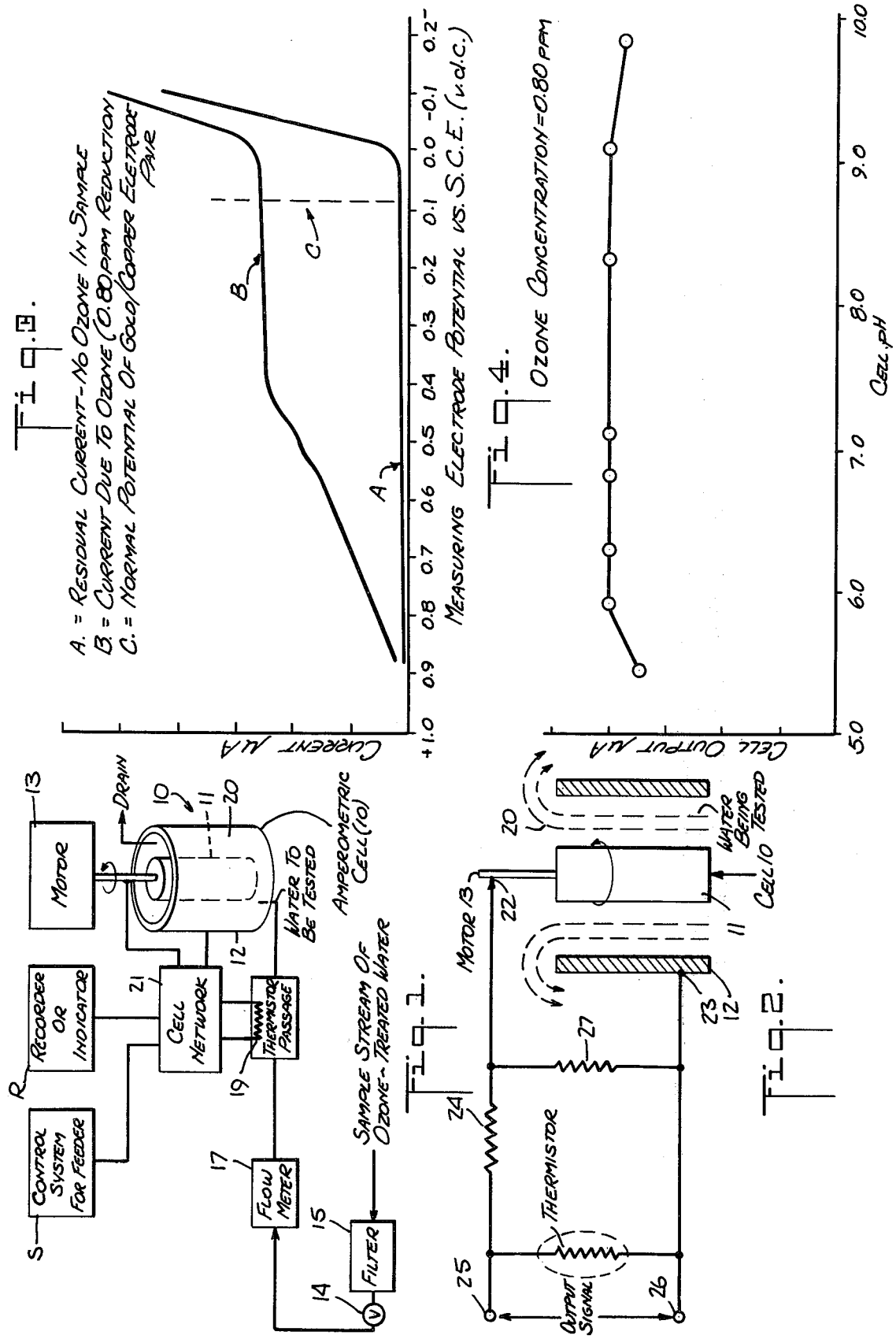

TECHNIQUE FOR CONTINUOUSLY ANALYZING THE CONCENTRATION OF OZONE DISSOLVED IN WATER

RELATED APPLICATION

This application is a continuation-in-part of the copending application Ser. No. 44,800 filed June 9, 1970, now abandoned.

BACKGROUND OF THE INVENTION

This invention relates generally to ozone testing, and in particular to a technique for continuously and accurately measuring the concentration of ozone dissolved in a liquid process stream.

Ozone is a triatomic form of oxygen which is produced by an electrical discharge through oxygen or by irradiation of oxygen by ultra-violet energy. At ordinary temperatures, ozone is highly unstable and quickly breaks down into a stable molecule of oxygen and a free oxygen atom. When this free atom of oxygen is blended with water, the water is converted to a peroxide valence which is a powerful oxidizing agent as well as a strong germicide.

Ozone is extensively used in the purification of drinking water, the treatment of sewage and industrial wastes, as well as in various chemical manufacturing processes. The unstable nature of ozone dictates its generation at the point of use, for it cannot be stored in containers in the manner of stable gases such as chlorine and oxygen.

While chlorination of water for purposes of sterilization is commonplace, in some instances chlorination is undesirable because of its influence on taste and flavor. Thus, in the making of beverages such as beer and soda, it is now the preferred practice to treat available water with ozone to ensure purity as well as flavor.

Ozone residual is the parts-per-million (ppm) of free ozone immediately available for reaction. To attain an effective germicidal action serving to destroy pathogens and all harmful bacteria and to react with oxidizable organic or inorganic chemical traces present in water, it is essential that the ozone concentration be in a predetermined range, such as 0.1 to 1 ppm. Below this range, the concentration is inadequate for its intended purpose, whereas an excessive concentration is wasteful. Moreover, since ozone is highly irritating and toxic even at low concentrations and is only slightly soluble in water, one must be careful to avoid introducing more ozone into the water than can be dissolved therein.

The standard laboratory technique for determining the concentration of ozone involves chemical analysis in a manual procedure which is time-consuming and at best produces only a spot check on concentration. It is known that dissolved ozone ($O_3$) reacts quantitatively with potassium iodide at pH 9.5 or higher to liberate iodine in direct proportion to ozone concentration. Determination of ozone, using the iodide reaction, is the usual laboratory method, wherein the liberated iodine may be titrated amperometrically. Hence, in the standard method, by maintaining the necessary pH level and measuring the liberated iodine, one may arrive at the ozone concentration.

SUMMARY OF THE INVENTION

In view of the foregoing, it is the primary object of this invention to provide a technique for ozone analysis which affords a continuous measurement of dissolved ozone concentration in a liquid stream.

More specifically it is an object of the invention to provide a technique wherein the process stream to be tested is sampled continuously in an amperometric cell wherein dissolved ozone produces a measurable current flow proportional to ozone concentration.

Among the significant advantages of the invention are that the electrical current yielded by the amperometric cell, which is proportional to ozone concentration, may be recorded to monitor ozone concentration, and the current may also be used to effect automatic control of ozone production to maintain the ozone concentration within the desired range. Also the analyzer in accordance with the invention is substantially insensitive to the pH level of the water.

Also an object of the invention is to provide a lowcost technique for ozone analysis which is reliable and efficient and affords accurate indications of ozone concentration.

Briefly stated, these objects are accomplished in a technique which employs an amperometric cell constituted by a rotating cathode formed of a noble metal concentrically disposed within a stationary anode, a sample stream of ozone-treated water being directed at a predetermined flow rate through the annular passage between the electrodes. In the absence of dissolved ozone, the cathode is polarized, but in the presence thereof, depolarization takes place to cause an electrical current to flow in the cell, which is proportional to the concentration of ozone in the water. The current is detected and indicated to provide a reliable and continuous reading of ozone concentration.

OUTLINE OF THE DRAWING

For a better understanding of the invention, as well as other objects and further features thereof, reference is made to the following detailed description to be read in conjunction with the accompanying drawing, wherein:

FIG. 1 is a schematic diagram of an ozone analyzer for carrying out a technique in accordance with the invention;

FIG. 2 schematically shows the amperometric cell included in the analyzer and its associated network;

FIG. 3 is a graph showing the relationship between ozone concentration and cell output as the potential of the cathode is changed; and FIG. 4 is a graph showing the insensitivity of the cell to pH within a given pH range.

DESCRIPTION OF THE INVENTION

Referring now to FIG. 1, the technique for ozone analysis in accordance with the invention makes use of an amperometric cell, generally designated by numeral 10. The cell is constituted by a cathode electrode 11, concentrically disposed within an anode 12, the cathode being rotated at high speed at a rate greater than 1000 RPM by a motor 13, the position of the anode being stationary. In the amperometric cell, a measurable electric current flow is produced as a result of the direct electrochemical reduction of dissolved ozone, the current flow being proportional to ozone concentration.

A sample stream from an ozone-treated water supply to be continuously analyzed is fed into cell 10 through a control valve 14 in the input thereof. The valve is placed in the line after a suitable mechanical filter 15, to remove particulate matter from the stream.

From valve 14, the liquid goes through a flowmeter 17 into a passage 18 having a thermistor 19 disposed therein, this passage leading to the input at the bottom of cell 10. In the cell, the sample stream passes upwardly through the annular space 20 between cathode 11 and anode 12, the liquid at the top flowing out of the cell to drain. Since flow rate significantly affects the output of the cell, the cell is supplied with liquid at a predetermined flow rate such as a rate of one-tenth of a liter per minute, the cell being calibrated at this rate.

The cathode and anode of the cell are connected to an electrical network generally designated by numeral 21, which includes thermistor 19, the circuit yielding a signal whose magnitude depends on the ozone concentration of water passing through the cell. The signal produced by network 21 is applied to an indicator or a potentiometric recorder R, or any other form of recording instrument, to provide a continuous record of ozone concentration. The signal may also be applied to an automatic control system S for comparison with a reference value to regulate the ozone-producing system to maintain a desired ozone concentration in the water.

As shown in FIG. 2 rotating cathode 11, which is the measuring electrode, is preferably fabricated of a noble metal such as gold. Anode 12 is formed of a material such as copper, which produces a potential of such sign and magnitude in the liquid that its combination with the gold cathode potential results in a spontaneously acting cell.

The output of cell 10 is taken from between a spring-loaded brush 22 engaging a ring on the shaft of motor 13 rotating the cathode, and a fixed contact 23 connected to the anode. Motor 13 operates at high speed, such as at 1650 r.p.m., whereby the polarization and depolarization cathode actions are uniformly distributed on the cathode surface. Brush 22 is connected through a precision resistor 24 to one output terminal 25, the other output terminal 26 going directly to anode contact 23. A second precision resistor 27 is connected between brush 22 and contact 23, whereas the thermistor 19 is shunted across the output terminals. In operation, current flowing through resistor 27 as a result of cell activity develops a voltage thereacross, the value of this voltage at the output terminals being corrected by thermistor 19.

Amperometric cells inherently possess a temperature coefficient that depends on electrode reaction kinetics. Since seasonal water-temperature variations are inevitably present in water installations calling for ozone measurement, it is essential that the output of the cell be compensated for such variations. Since the thermistor is shunted across the output of the cell circuit 21, it serves to cancel out the effect of temperature on the output of the cell network.

The composition of the cathode is such that polarization thereof occurs in the absence of ozone in the sample. Polarization renders the cell non-conductive and substantially no current flows therethrough. The existence of the smallest trace of ozone in the sample stream acts to depolarize the cathode, giving rise to the following reaction:

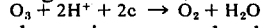

At the stationary anode, the following reaction takes place:

Three-electrode polarography may be used to determine the conditions required of the cell using gold/copper electrodes. In this technique, a stable reference electrode, a saturated calomel electrode (SCE), is included in the cell in contact with the sample solution. An external voltage is applied between the gold measuring electrode 11 and the anode 12, and the potential of the measuring electrode is varied and measured with respect to the SCE.

In the absence of ozone in the cell, as the cathode potential is varied from +0.9 VDC vs. SCE, to 0.0VDC, an extremely small constant current flow (residual current) will be observed in the external circuit. Dissolved ozone is added to the cell and again the cathode potential is varied from +0.9V to 0.0V. In this case, a steadily increasing current flow will be observed until the cathode potential reaches approximately +0.4V. The current flow then remains constant until the potential reaches 0.0V.

Experiments show that the current flow over the electrode potential range, +0.4 to 0.0 vs. SCE, is proportional to ozone concentration in the cell. Thus in the cell, a potential is maintained in the cathode at a level resulting in a proportional relationship between the concentration of the ozone being measured and the resultant current flow. When short-circuited, the gold-copper electrode pair forms a galvanic cell in which the potential of the gold electrode is approximately +0.10V with respect to the copper electrode and also +0.10V compared to the SCE. At this potential ozone is reduced, yielding a current proportional to concentration.

FIG. 3 shows the current/voltage described above. Curve A shows the residual current when no ozone is present in the sample, and it will be seen that at the normal potential of the gold/copper electrode pair (about 0.1V), there is virtually no current flow. But as evident from curve B, when ozone is present (0.80 ppm), a significant current flows.

The residual current flow observed in the current-/voltage curve A is the result of a phenomenon known as the electric double layer at the electrode surface. In the absence of an oxidizable or reducible substance, it has been found that a finite current flows when the potential of an electrode is varied. The current is non-Faradaic since it does not result from an electron transfer reaction. The current flow is the result of the redistribution of ionic charges in the electrical double layer which occurs when the electrode potential is changed.

When dissolved ozone is present in the cell and the potential of the measuring electrode is +0.90V vs. SCE, there is almost no current flow. As the measuring electrode potential is slowly shifted in a negative direction, there is observed a steady increase in cathodic current resulting from the reduction of ozone. The current flow reaches a maximum level at about +0.40V and remains constant until the electrode potential is approximately 0.0V (vs. SCE), when a further increase in current flow is observed due to the reduction of dissolved oxygen in the sample. The maximum current for the reduction of ozone is called the limiting current. The magnitude of the limiting current is a function of the rate of mass-transport of ozone from the solution to the electrode surface and is proportional to the concentration of ozone in the solution.

It has been found that variation of cell pH between approximately 6.0 and 9.0 has no appreciable effect on the current/voltage relationship, nor is pH control necessary to maintain electrode sensitivity in normal water samples. FIG. 4 shows the effect of pH on cell current when a copper/gold cell is operating galvanically. It will be evident from the curve that, between 6.0 and 9.0 cell pH, the cell output current remains at a steady level. Hence in practice it is not necessary to stabilize the pH level.

Other electrode materials, either forming a galvanic type cell or using an impressed voltage to control electrode potential, may be used to measure ozone concentration. For example, the measuring electrode may be formed of graphite or stainless steel, and the anode may be made of any material which, when short-circuited, will cause the measuring electrode to assume a favorable potential with respect to SCE for reduction of ozone. Also, a combination of similar or dissimilar electrode materials may be used, such as platinum and zinc, if an external voltage source is employed to maintain the proper potential on the measuring electrode. In this instance, the impressed potential must be such as to cause the platinum electrode to assume a potential at the plateau portion of the curve B in FIG. 3.

In addition to the technique described above, ozone can be measured with the same amperometric cell by making use of the following reaction:

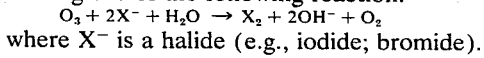

where $X^-$ is a halide (e.g., iodide; bromide).

The liberated halogen concentration is in direct proportion to ozone concentration and generates a current in the cell proportional to ozone. However, direct ozone measurement is preferred over the halogen reaction method for continuous analysis, since the direct reduction of ozone does not require the addition of any chemicals to the sample. As pointed out previously, determination of ozone concentration using the iodide reaction technique is a standard laboratory method. This laboratory method is of value in calibrating the continuous ozone analyzer.

In continuous operation over a thirty-day period, the ozone analyzer of the type shown in FIGS. 1 and 2 was found to give excellent reproducible results as the ozone concentration in the sample was varied over the range of 0 to 1 ppm. Analyzer results during this test period were well within ± 2% of full scale; i.e., ± 0.02 ppm ozone.

While there have been shown and described preferred embodiments of the ozone analyzing technique, it will be appreciated that many changes and modifications may be made therein without, however, departing from the essential spirit of the invention.

We claim:

1. A technique for continuously analyzing the concentration of ozone in an ozone-treated water supply without the use of chemicals, said technique comprising the steps of:
   A. conducting a sample of water from said supply at a predetermined flow rate into the annular space which exists in an amperometric cell formed by a cathode disposed within a tubular anode;
   B. rotating said cathode at a speed at which polarization and depolarization actions are uniformly distributed on the cathode surface, said cathode being polarized in the absence of ozone in the sample to produce substantially no current flow in said cell and being directly depolarized by ozone to produce a current flow therein which depends on the concentration of ozone;
   C. maintaining a potential on said cathode at a level resulting in a proportional relationship between the concentration of ozone and the resultant current flow; and
   D. measuring said current flow to indicate the concentration of ozone.

2. A technique as set forth in claim 1, wherein said cathode is made of a noble metal.

3. A technique as set forth in claim 1, further including the steps of sensing the temperature of said water sample and correcting the current flow indication to compensate for the effect of temperature thereon.

4. A technique as set forth in claim 1, wherein said cathode is rotated at a rate greater than 1000 r.p.m.

5. A technique as set forth in claim 1, wherein said cathode is made of platinum and said anode is made of zinc.

* * * * *